United States Patent
Fischer et al.

(10) Patent No.: US 10,537,522 B2
(45) Date of Patent: Jan. 21, 2020

(54) BREWING APPARATUS HAVING A PHARMACEUTICAL, HOLISTIC OR MEDICINAL TREATED BREWING SCREEN OR FILTER

(71) Applicant: GGCC, Inc., Newport Beach, CA (US)

(72) Inventors: Kristy A. Fischer, Newport Beach, CA (US); Christopher M. Haase, Irvine, CA (US)

(73) Assignee: GGCC, Inc, Newport Beach, CA (US)

( * ) Notice: Subject to any disclaimer, the term of this patent is extended or adjusted under 35 U.S.C. 154(b) by 594 days.

(21) Appl. No.: 15/179,527

(22) Filed: Jun. 10, 2016

(65) Prior Publication Data

US 2016/0361256 A1   Dec. 15, 2016

Related U.S. Application Data (60) Provisional application No. 62/174,224, filed on Jun. 11, 2015.

(51) Int. Cl.
| | |
|---|---|
| *A61K 9/00* | (2006.01) |
| *A61K 47/44* | (2017.01) |
| *A61K 47/46* | (2006.01) |
| *A47J 31/06* | (2006.01) |
| *A61J 3/00* | (2006.01) |

(52) U.S. Cl.
CPC ............ *A61K 9/0095* (2013.01); *A47J 31/06* (2013.01); *A61J 3/00* (2013.01); *A61K 47/44* (2013.01); *A61K 47/46* (2013.01)

(58) Field of Classification Search
CPC .... A47J 31/06; A47J 31/0615; A47J 31/0642; A47J 31/0663; A61J 3/00; A61J 3/002; A61J 3/07; A61J 3/077; A61K 47/44; A61K 47/46; A61K 9/0095
USPC .................. 426/74, 76, 86, 89; 99/295, 298
See application file for complete search history.

(56) References Cited

U.S. PATENT DOCUMENTS

| | | | |
|---|---|---|---|
| 2003/0032945 A1* | 2/2003 | Jayaraman | A61K 9/009 604/890.1 |
| 2013/0340626 A1* | 12/2013 | Oh | B65D 85/8043 99/295 |
| 2015/0147359 A1* | 5/2015 | Egberg | A61K 9/10 424/400 |

* cited by examiner

*Primary Examiner* — Dana Ross
*Assistant Examiner* — James F Sims, III
(74) *Attorney, Agent, or Firm* — Baker Hostetler (57) ABSTRACT

The present disclosure provides for brewing apparatus, such as a disposable brewing pod, filter, beverage screen, or tea bag, treated with an oil-based solution comprising a lipid component; an emulsifier; and a pharmaceutical, holistic, or medical component. Brewing apparatus may be sprayed with a spray gun, such as a high volume low pressure spray gun, a precision bottle-top dispenser, or an automatic apparatus configured to apply an oil-based solution to the brewing apparatus. The brewing apparatus may be filled with a product to be brewed and packaged for individual use. The present disclosure additionally provides for a brewed drinkable product produced using brewing apparatus treated with an oil-based solution comprising a lipid component; an emulsifier; and a pharmaceutical, holistic, or medical component. The end product may be a hot or cold product.

3 Claims, 12 Drawing Sheets

BREWING APPARATUS HAVING A PHARMACEUTICAL, HOLISTIC OR MEDICINAL TREATED BREWING SCREEN OR FILTER

CROSS-REFERENCE TO RELATED APPLICATIONS

This application claims priority to U.S. Provisional Application No. 62/174,224, which was filed on Jun. 11, 2015. The contents of U.S. Provisional Application No. 62/174,224 in their entirety are hereby incorporated by reference.

BACKGROUND

The current disclosure relates to brewing screens or filters (or brewing apparatuses, such as disposable brewing cups or pods containing such brewing screens or filters) for brewing coffees, teas, drinks, soups and the like.

SUMMARY

It is an aspect of the current disclosure to provide a beverage (or fluidic food) brewing apparatus prepared by a process including the steps of: obtaining at least one of a brewing filter or screen; preparing an oil-based solution including: an edible oil carrier, a food grade emulsifier and at least one of a pharmaceutical, holistic or medicinal component additive; and spraying (or otherwise applying by dipping, soaking, and the like, for example) the oil-based solution onto the brewing filter or screen. In a more detailed embodiment, the process further includes the step of filling a product to be brewed into the sprayed brewing filter or screen. In yet a further detailed embodiment, the process further includes the step of enclosing the filled brewing filter or screen into a packaging container.

In an embodiment, the packaging container may be, for example, a disposable brewing cup for a single-cup brewing system. In an embodiment, the product to be brewed may include coffee grinds, tea leaves, drink powder, crystallized drink, and/or soup powder. In an embodiment, the brewing filter or screen may be a coffee filter or a tea bag.

In an embodiment, the packaging container may be, for example, a drink flavoring mix or syrup for a home water-carbonation machine, soda syphon, or other machine capable of forcing pressurized carbon dioxide gas into a container containing liquid to dissolve the gas into the liquid. Such drink flavoring mixes may come in single-use containers. In an embodiment, the product to be brewed may include sparkling water, homemade sodas and colas, flavored sparking waters, and like liquid products. In reference to cold drinks, the term product to be brewed is still used to refer to the preparation of a final liquid product for consistency with the rest of the disclosure, notwithstanding that this may not be a typical use of the word brew.

In an embodiment, the step of preparing the oil-based solution includes heating the oil-based solution to a temperature substantially in the range of approximately 100° F. to approximately 180° F. In an embodiment, the step of preparing the oil-based solution includes stirring or agitating the oil-based solution for a time period of at least one to two minutes. In an embodiment, the oil-based solution includes: 50-80% of a food grade lipid component; 1-14% of an emulsifier and stabilizer component; 1-6% of an emulsifier component; and 4.8-30% of a pharmaceutical, holistic or medicinal component. In an embodiment, the spraying step sprays the brewing filter or screen with 0.26-0.75 grams of the oil-based solution.

In an embodiment, the oil-based solution includes: 50-80% of a lipid; 1-14% of a polysorbate; 1-6% of a sorbitan stearate; and 4.8-30% of a pharmaceutical, holistic or medicinal component.

In an embodiment, the oil-based solution may include: 50-80% of a lipid; 1-20% of an extract of *Quillaja saponaria*; and 4.8-30% of a pharmaceutical, holistic or medicinal component.

In an embodiment, the oil-based solution may include: 50-80% of a lipid; 1-14% of a polysorbate; 1-6% of an extract of *Quillaja saponaria*; and 4.8-30% of a pharmaceutical, holistic or medicinal component.

In an embodiment, the oil-based solution may include: 50-80% of a lipid; 1-14% of an extract of *Quillaja saponaria;* 1-6% of a sorbitan stearate; and 4.8-30% of a pharmaceutical, holistic or medicinal component.

It is another aspect of the current disclosure to provide a beverage (or fluidic food) brewing apparatus that includes a brewing filter/screen, where the brewing filter/screen has with an oil-based solution applied thereon, and where the oil-based solution includes: an edible oil carrier, a food grade emulsifier and at least one of a pharmaceutical, holistic or medicinal component additive. As described herein, a brewing filter/screen may be used in the preparation of both hot and cold fluid products, for example, as part of single-serve coffee machines and or single-use flavorings for home water-carbonation machines. In an embodiment, the brewing apparatus further includes a product to be brewed (including, for example, coffee grinds, tea leaves, powdered drink flavoring, etc.) contained within the brewing filter/screen. In a further detailed embodiment, the brewing apparatus further includes a packaging container enclosing the filled brewing filter or screen. In yet a further detailed embodiment, the packaging container includes a disposable brewing cup for a single-cup brewing system. In an embodiment, the brewing filter/screen may be positioned near the cap or opening of a container, and a liquid within the container may be poured through the brewing filter/screen before exiting the container. In an embodiment, the brewing filter/screen may be a "sock" form to fit around a nozzle of a home water-carbonation nozzle or a dispensing area of a commercial single-serve liquid dispensing unit.

In an embodiment, the product to be brewed using the brewing apparatus is coffee grinds, tea leaves, drink powder, crystallized drink, and/or soup powder. In an embodiment, the product to be brewed is a flavoring or liquid concentrate to be poured into a diluting liquid, for example, home-prepared carbonated water. In an embodiment, the brewing filter/screen of the brewing apparatus is a coffee filter or a tea bag. In an embodiment, the oil-based solution applied to the filter/screen includes: 50-80% of a food grade lipid component; 1-14% of an emulsifier and stabilizer component; 1-6% of an emulsifier component; and 4.8-30% of a pharmaceutical, holistic or medicinal component. In an embodiment the brewing filter/screen of the brewing apparatus includes 0.26-0.75 grams of the oil-based solution applied thereon.

BRIEF DESCRIPTION OF THE DRAWINGS

The foregoing and other features of the present disclosure will become more fully apparent from the following description, taken in conjunction with the accompanying drawings. These drawings depict only several embodiments in accordance with the disclosure and are, therefore, not to be considered limiting of its scope. The disclosure will be described with additional specificity and detail through the use of the accompanying drawings.

In the drawings.

DETAILED DESCRIPTION

The current disclosure relates to brewing screens or filters (or brewing apparatuses, such as disposable brewing cups or pods containing such brewing screens or filters) for brewing coffees, teas, drinks, soups and the like. Brewing screens or filters may also be placed near the cap or opening of a container containing a flavoring liquid, for example, flavorings used to flavor home-prepared carbonated water. Exemplary brewing cups or pods include those marketed under the Keurig™, Nespresso™, or Verismo™ brewing systems and flavoring containers marketed under the SodaStream™ systems.

In an exemplary embodiment, such brewing screens or filters are prepared by a process of spraying and/or saturating the screen or filters by airbrushing them, using commercial food manufacturing spraying equipment (for example, handheld spraying guns, industrial spraying machines via conveyance, pharmaceutical-grade dosing pumps, and precision bottle-top dispensers), with a formulation containing: medicinal, pharmaceutical, or holistic (for example, herbal oils, tinctures and concentrates) additives blended into an edible oil carrier with food grade emulsifiers such as poloysorbate 60, sorbitan monostearate, and/or one or more extracts of *Quillaja saponaria*, including, for example, a powderized form of the inner bark of the *Quillaja saponaria* plant. Other emulsifiers or stabilizers may be used and are envisioned by the present disclosure, including other polysorbates, such as polysorbate 20, polysorbate 40, or polysorbate 80. The difference in these polysorbates may depend on the type of fatty acid associated with the polyoxyethylene sorbitan portion of the molecule. *Quillaja saponaria* extract is a natural, generally-recognized-as-safe surfactant ingredient available in food-grade preparations. This material is rich in saponins and sapogenins, contributing to its utility as a surfactant (and, therefore, an emulsifier and stabilizer in foods). *Quillaja saponaria* extract may be used as a substitute for a non-ionic surfactant. One skilled in the art will recognize that quantity adjustments may need to be made depending on the particular emulsifier and/or stabilizer (if required) used.

The present disclosure generally refers to spraying equipment or spraying apparatus as the equipment that applies the oil-based solution to the coffee brew pod filters, tea bags, conventional filters, screens for use in a concentrated flavoring or syrup container, or the like, regardless of whether the equipment or apparatus actually forms a "spray" or mist. Example spraying apparatus includes handheld spray guns (including commercial spray guns designed for food use and high-volume, low-pressure spray guns), precision bottle-top dispensers, pharmaceutical-grade dosing pumps with analog and/or digital measurement tools, and automatic systems. The precision bottle-top dispensers and pharmaceutical-grade dosing pumps may be autoclavable for use with sterile reagents and capable of dispensing a wide variety of solutions. Automatic systems be particularly useful in preparing screens and filters on a large scale and may include automatic spray nozzles, a spray controller, a spray manifold, a conveyor system, and infrared beam transmitters and receivers to assist in accurately controlling the spray. In automatic systems, the oil-based solution may be stored in holding tanks, vats, or hoppers, which may provide quick availability of solution to the spray system. Cycling via conveyance under controlled timing using infrared beams, one or more carrier trays and/or individual cups, containers, packages, bottles, bags, screens, or filters may pass under automatic precision spray control nozzles or pharmaceutical-grade dosing pump nozzles driven by pistons and cylinders, which may be electrically, digitally, or mechanically actuated to turn on and off quickly. This may deposit a quick, accurate dose of for example, between 0.26-0.75 grams of a prepared oil-based solution, thereby saturating (either fully or partially) each individual cup, filter, tea bag, bottle, or pod. The oil may be stored above in a holding tank, vat, reservoir, or hopper which may be pumped to the nozzles and/or depositing heads. The oil may be heated.

Such prepared screens or filters can then be used for brewing hot beverages (coffees, teas, hot chocolates, ciders and other flavors). The prepared screens or filters may also be incorporated into brewing cups or pods, including those marketed under the Keurig™, Nespresso™, or Verismo™ brewing systems. Of course, other various single cup brewing system, coffee and tea filter pods, standard coffee filters in various shapes and sizes for all home drip brewing machines, and paper or fabric tea bags being sold on the market may also be treated with prepared by such a process. Such prepared screens or filters may also be used to prepare cold beverages, such as flavored sparkling water, cold-brew coffee, cold-brew tea, soda, and the like. In an embodiment, the brewing filter/screen may be a "sock" form to fit around a nozzle of a home water-carbonation nozzle or a dispensing area of a commercial single-serve liquid dispensing unit In one exemplary production flow, a batch (e.g., 4000) of filters (e.g., filters for single brewing cups, pods, tea bags or standard paper or fabric coffee filters) are sprayed with a premeasured amount of the oil-based solution to ensure that both accurate and repeatable dosages on all finished goods is achieved. If such filters are to be used with disposable brewing cups or pods (such as those marketed under the Keurig™, Nespresso™, or Verismo™ brewing systems), the sprayed filters may then be inserted into the brewing cup or pod container or harness. Coffee beans may then be processed in an industrial coffee grinder and pre-set amounts of such grinds may be deposited into the sprayed filter contained in the brewing cup or pod container or harness. Once filled, the brewing cup pod or harness may be sealed (for example, with foil or other puncturable substrate covering the top of the cup or harness) and then the sealed cups or pods may be packed in master case box (e.g. 48 cups or pods per box). If such screens are to be used with limited-use flavoring containers containing concentrated liquids or syrups (such as those used in connection with SodaStream™ systems), the sprayed screens may be inserted (and/or fixed) near the opening or cap of the container such that the liquid passes through the screen when poured from the container. The liquid in the container may be present in the container before the screen is inserted, and a cap or other sealing mechanism may then be applied to close the system.

Of course, the product to be filled into the sprayed filters is not limited to coffee. Other drink products or fluidic food products may also be filled into the sprayed filters. Such alternative products may include, without limitation: tea leaves, spices, herbal tea components, drink powder, crystallized drink powder or granules, soup powder, condensed and/or dried drink or soup granules or blocks. Such products can be brewed to make hot or cold drinks, soups, sauces, gravies, flavored carbonated waters, and the like.

The oil-based solutions may be compiled in various ways. Variations may be made based on many factors, including dosage requirements of the pharmaceutical, holistic, or medicinal additive in relation to a user. Variations may also be made based on the lipid component to be used. For example, coconut oil, hemp oil, vegetable oil, soybean oil, palm kernel oil, medium-chain triglycerides, or combinations thereof may be used. Further variations may be made depending on the emulsifier and/or stabilizer (if required) used. In an embodiment, the oil-based solution includes: 50-80% of a lipid; 1-14% of a polysorbate; 1-6% of a sorbitan stearate; and 4.8-30% of a pharmaceutical, holistic or medicinal component. In an embodiment, the oil-based solution may include: 50-80% of a lipid; 1-20% of an extract of *Quillaja saponaria*; and 4.8-30% of a pharmaceutical, holistic or medicinal component. In an embodiment, the oil-based solution may include: 50-80% of a lipid; 1-14% of a polysorbate; 1-6% of an extract of *Quillaja saponaria*; and 4.8-30% of a pharmaceutical, holistic or medicinal component. In an embodiment, the oil-based solution may include: 50-80% of a lipid; 1-14% of an extract of *Quillaja saponaria*; 1-6% of a sorbitan stearate; and 4.8-30% of a pharmaceutical, holistic or medicinal component. The following table provides several exemplary batch formulations for the oil-based solution to be sprayed on the filter or screen:

| Percent (Batch 1X) | Ingredients | Batch 1X (grams) | Batch 2X (grams) | Batch 4X (grams) | Batch 8X (grams) |
| --- | --- | --- | --- | --- | --- |
| 77.6 (range 50-80%) | Lipid Component (e.g., coconut oil, hemp oil, vegetable oil, soybean oil, palm kernel oil, or medium-chain triglycerides) | 1.009 g | 1.009 g | 1.009 g | 1.009 g |
| 13.9 (range 1-14%) | Emulsifier and Stabilizer (e.g., polysorbate 60 and gel, *Quillaja saponaria* extract) | 0.18 g | 0.18 g | 0.18 g | 0.18 g |
| 3.7 (range 1-6%) | Emulsifier (e.g., granular sorbitan stearate, *Quillaja saponaria* extract) | 0.048 g | 0.048 g0. | 0.048 g | 0.048 g |
| 4.8 (range 4.8-30%) | Pharmaceutical, holistic (herbal oil, tincture, and/or concentrate), or medicinal additive (dry or liquid) | 0.0625 g | 0.125 g | 0.25 g | 0.50 g |
| 100 | | 1.300 g | 1.362 g | 1.487 g | 1.737 g |

An exemplary process for preparing the oil-based solution is as follows. First, combine the ingredients (scaled as appropriate) and place in a heat-proof container. Second, heat the ingredients under low temperature, for example, over a water bath, a stove top, or in a warming oven. In an embodiment, the components are heated to a temperature ranging from 100° F. to 180° F. While heating, or after heating, the ingredients are mixed and/or agitated to ensure that the ingredients have adequately combined. In an embodiment, the components are stirred for 1-2 minutes. This step creates the oil-based solution. Third, pour the oil-based solution into a spraying apparatus holding tank or reservoir. In an embodiment, the spraying apparatus may be a handheld spray gun or an automatic spraying apparatus, including a high volume low pressure (HVLP) spray gun. In an embodiment, the spraying apparatus may be a precision bottle-top dispenser. Fourth, spray or dispense, using the spraying apparatus, each of the individual filters or screens with the oil-based solution. In an embodiment, between 0.26 to 0.75 grams (and, specifically, 0.27 grams) of the oil-based solution are sprayed onto the individual filters or screens. The filters or screens may be sprayed while seated in such brewing cups or pods or may be sprayed prior to inserting the filters or screens into such brewing cups or pods or concentrated flavoring containers.

The sprayed filters or screens may be filled with the product to be brewed as described above. In an embodiment, the sprayed filters or screens may be sold as sprayed filters or screens for consumers to add their own products to be brewed.

Figure 1A:
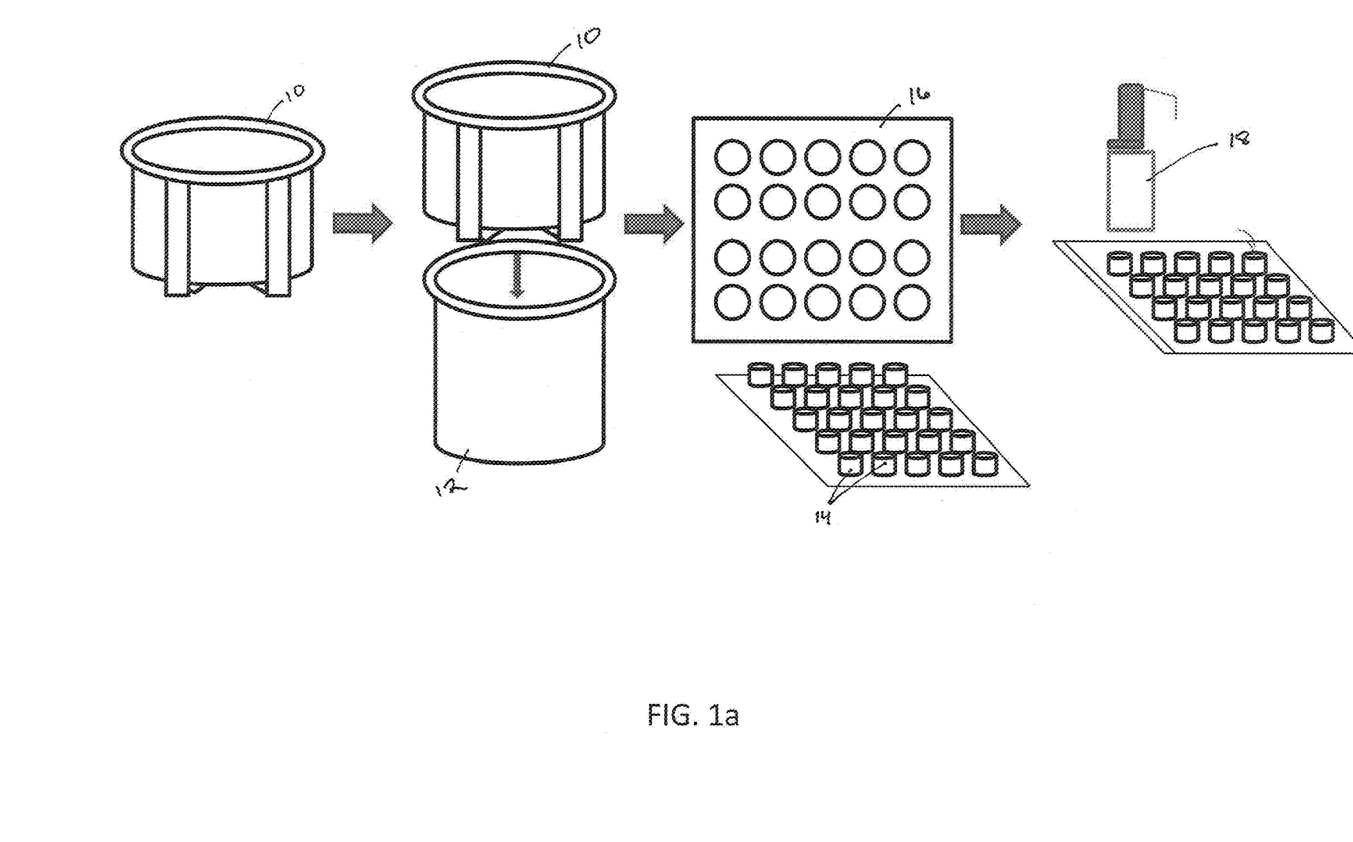
FIG. 1a illustrates a portion of an exemplary semi-automatic brewing pod production line.
Figure 1B:
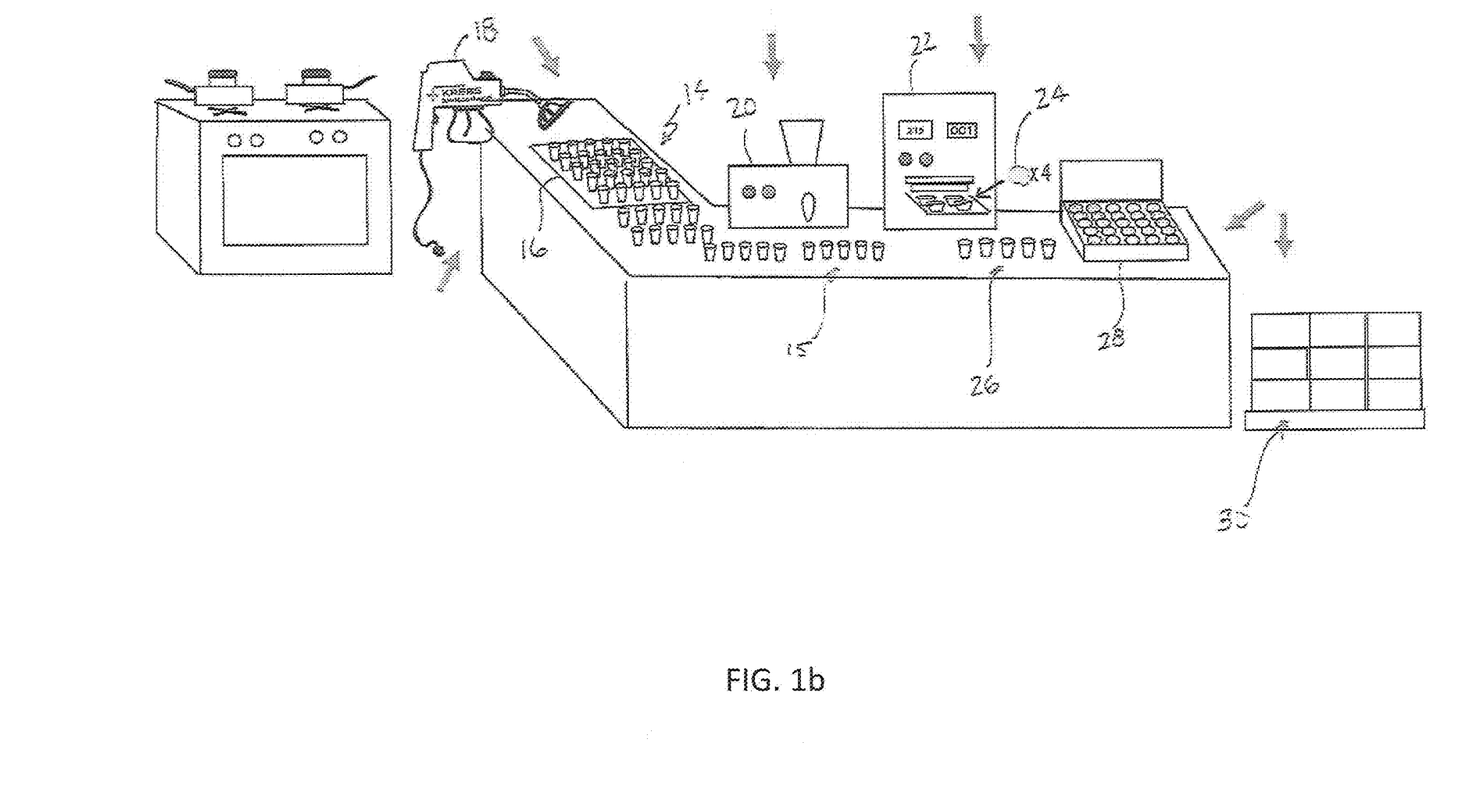
FIG. 1b illustrates an exemplary semi-automatic brewing pod production line.
Figure 1C:
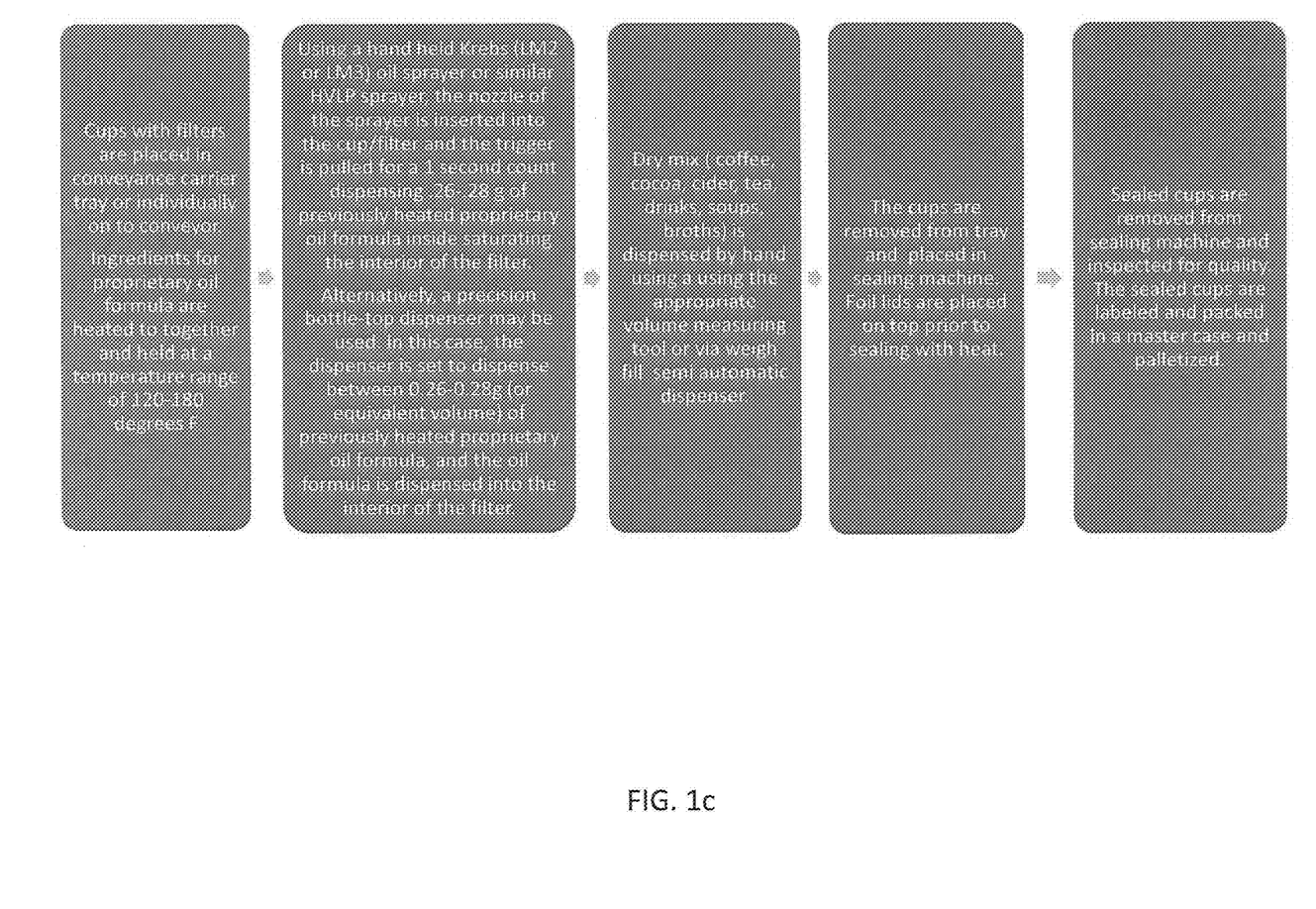
FIG. 1c is a flow chart describing the exemplary production lines of FIGS. 1a and 1b.

As shown in FIGS. 1a and 1b, an example disposable brewing pod semi-automatic production line is illustrated. FIG. 1c provides a flow chart of the process illustrated in FIGS. 1a and 1b. In an embodiment, disposable brewing pod filters 10 may be inserted into the filter container 12 to get a cup/filter 14. The cup/filter combinations 14 may be placed in a conveyance carrier tray 16 or individually on a conveyor. The oil-based solution may be prepared as discussed above. The oil-based solution may be placed in a holder or reservoir (e.g., the reservoir of a spraying apparatus). Then, using a spraying apparatus 18 (such as, for example, a Krebs brand LM2 or LM3), the nozzle of the spraying apparatus 18 may be inserted into the cup/filter 14 and the trigger may be pulled for a 1 second count, thereby dispensing 0.26-0.75 g of the oil-based solution and saturating the filter 10 within cup/filter 14. In an alternate embodiment, the spraying apparatus 18 may be a precision bottle-top dispenser. The precision bottle-top dispenser, as the spraying apparatus 18, could be pre-set to dispense between 0.26-0.75 g, for example, of the oil-based solution into the cup/filter 14 when toggled by a user. Dry product to be brewed (e.g., coffee, cocoa, cider, tea, drinks, soups, or broths) may be dispensed by hand using an appropriate volume measuring tool or via a weigh-fill semi-automatic dispenser 20. The filled cup/filter combinations 15 may be removed from the tray 16 (if used) and placed in a sealing machine 22. In sealing machine 22, foil lids 24 may be sealed over the top of the filled cup/filters 15. From there, the sealed cups 26 may be removed from the sealing machine and inspected for quality. The sealed cups 26 may then be labeled and packed in a master case 28 and palletized 30.

Figure 2A:
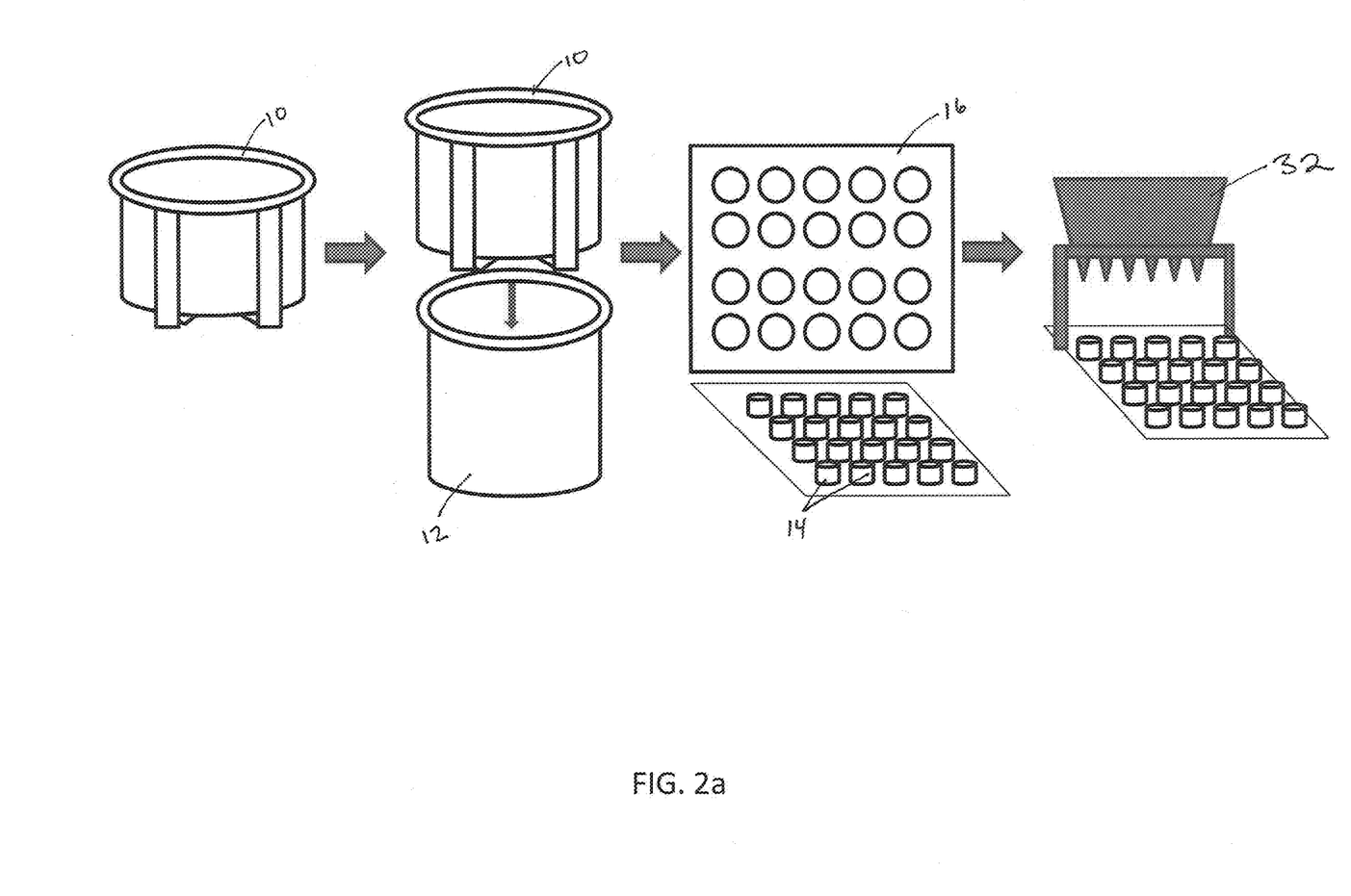
FIG. 2a illustrates a portion of an exemplary automatic brewing pod production line.
Figure 2B:
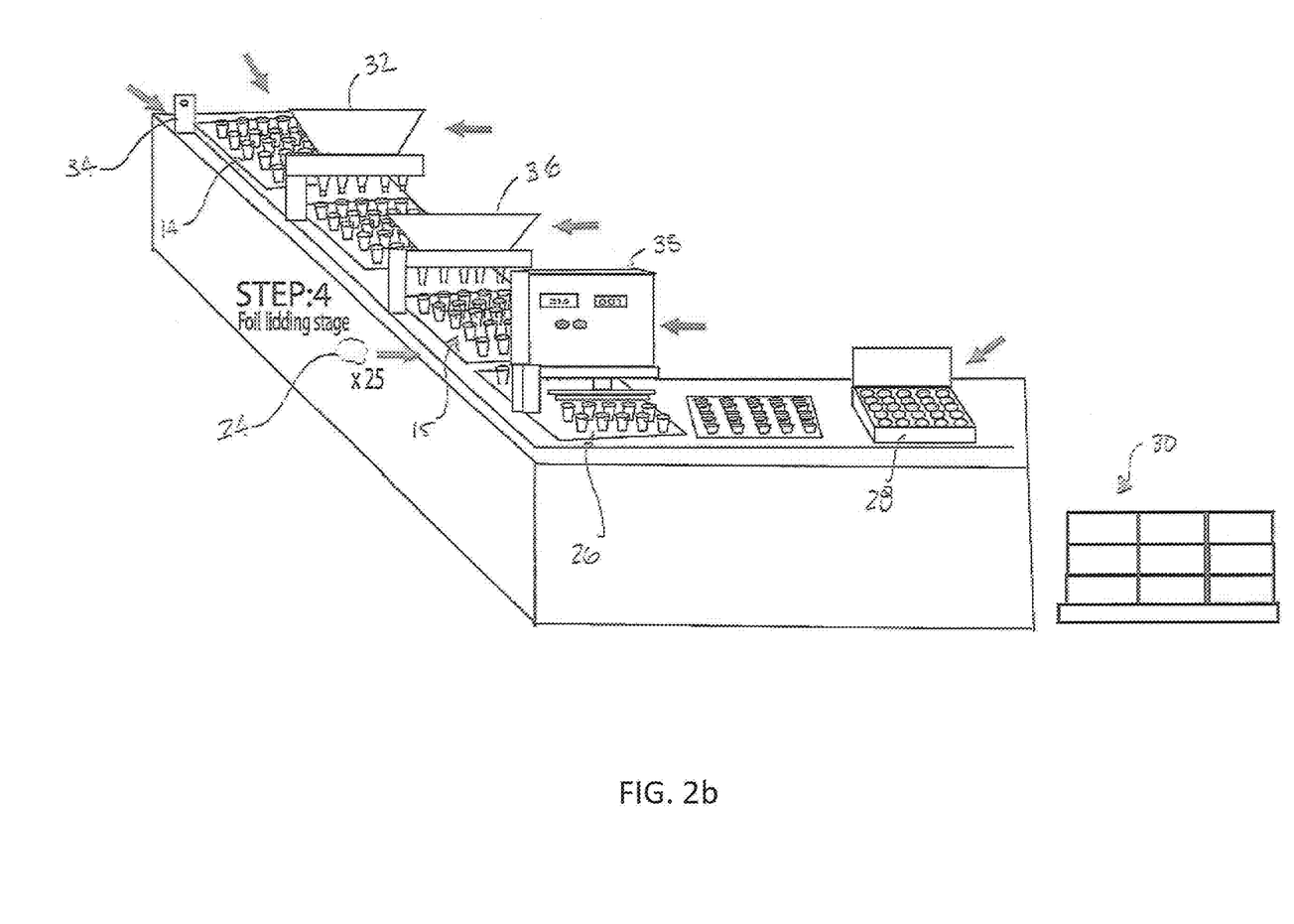
FIG. 2b illustrates an exemplary automatic brewing pod production line.
Figure 2C:
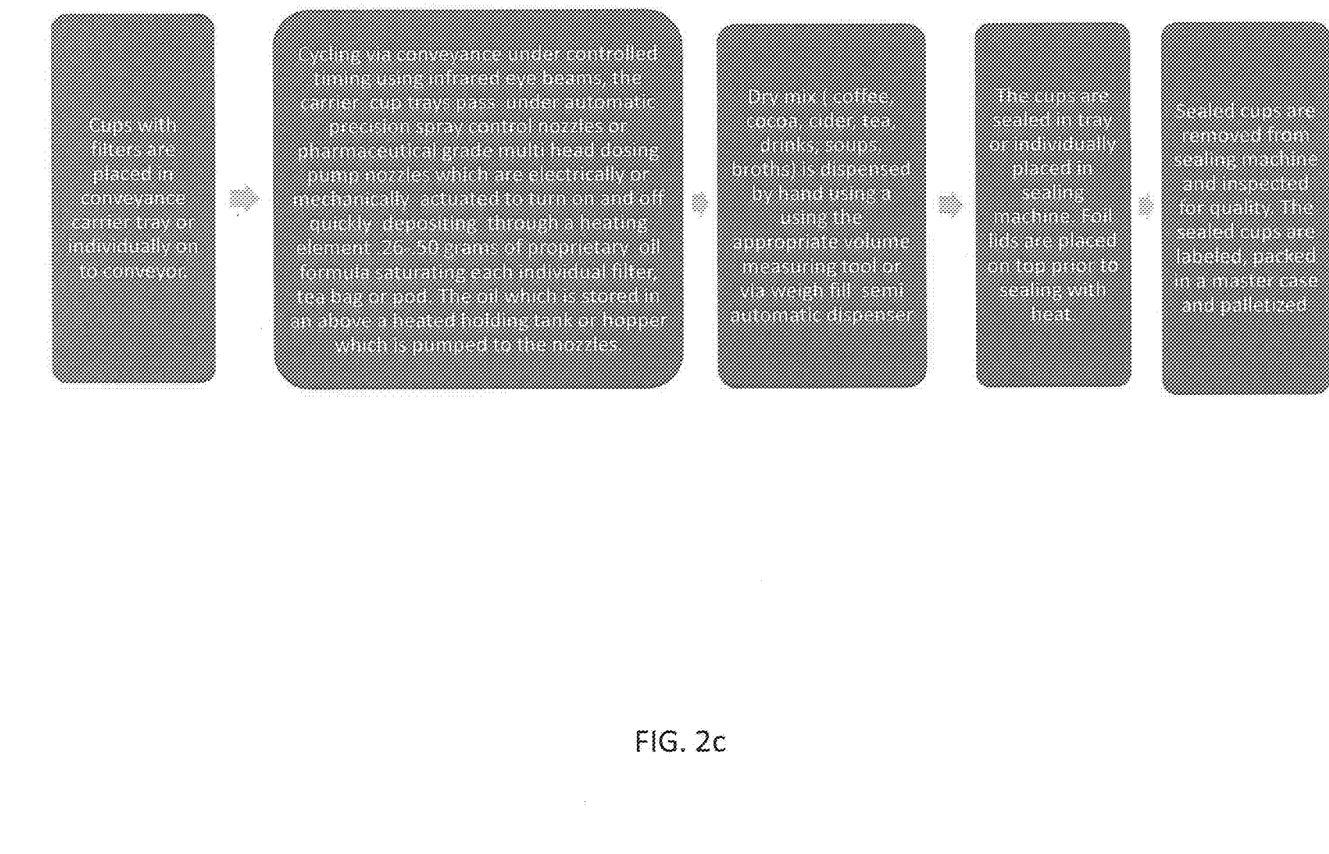
FIG. 2c is a flow chart describing the production line of FIGS. 2a and 2b.

As shown in FIGS. 2a and 2b, an example disposable brew pod automatic production line is illustrated. FIG. 2c provides a flow chart describing the production line of FIGS. 2a and 2b. Disposable brew pod filters 10 may be inserted into the disposable brew pod filter container 12 to get a cup/filter 14. The cup/filter combinations 14 may be placed in a conveyance carrier tray 16 or individually on a conveyor. The oil-based solution may be prepared as discussed above. Using an automatic precision spray control depositor 32, the oil-based formulation at the proper temperature and application rate may be applied to the filters 10 in the cup/filter combinations 14. An infrared eye timing beam 34 may be used to signal the electrically actuated nozzles of the depositor 32 at an appropriate timing rate based upon a sensed movement of the conveyor. Dry product to be brewed (e.g., coffee, cocoa, cider, tea, drinks, soups, or broths) may be dispensed using an automatic dispenser 36. The filled cup/filter combinations 15 may be removed from the tray 16 (if used) and placed in an automatic sealing machine 38, in which foil lids 24 are sealed over the top of the filled cup/filters 15. From there, the sealed cups 26 may be removed from the sealing machine and inspected for quality. The sealed cups 26 may then be labeled and packed in a master case 28 and palletized 30.

Figure 3A:
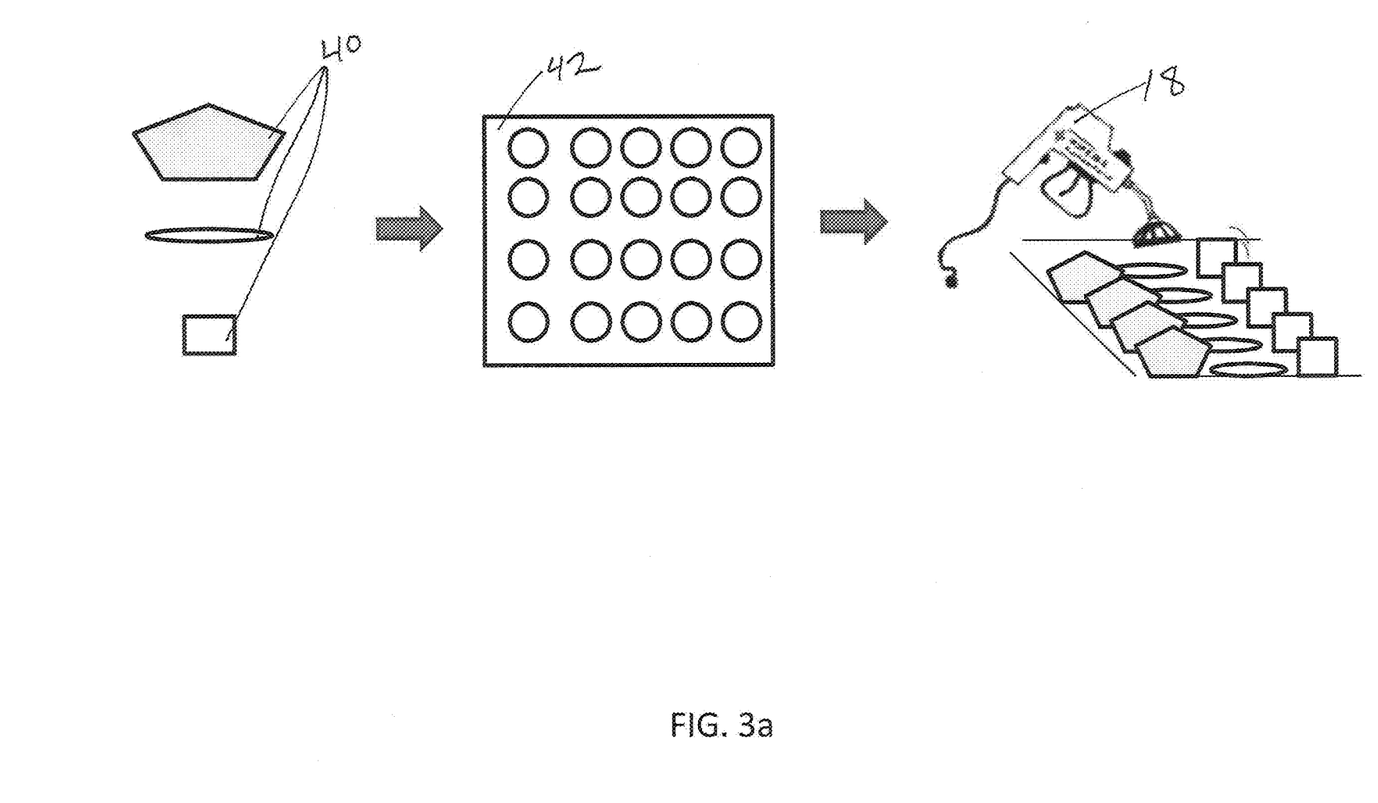
FIG. 3a illustrates a portion of an exemplary manual brewing apparatus production line.
Figure 3B:
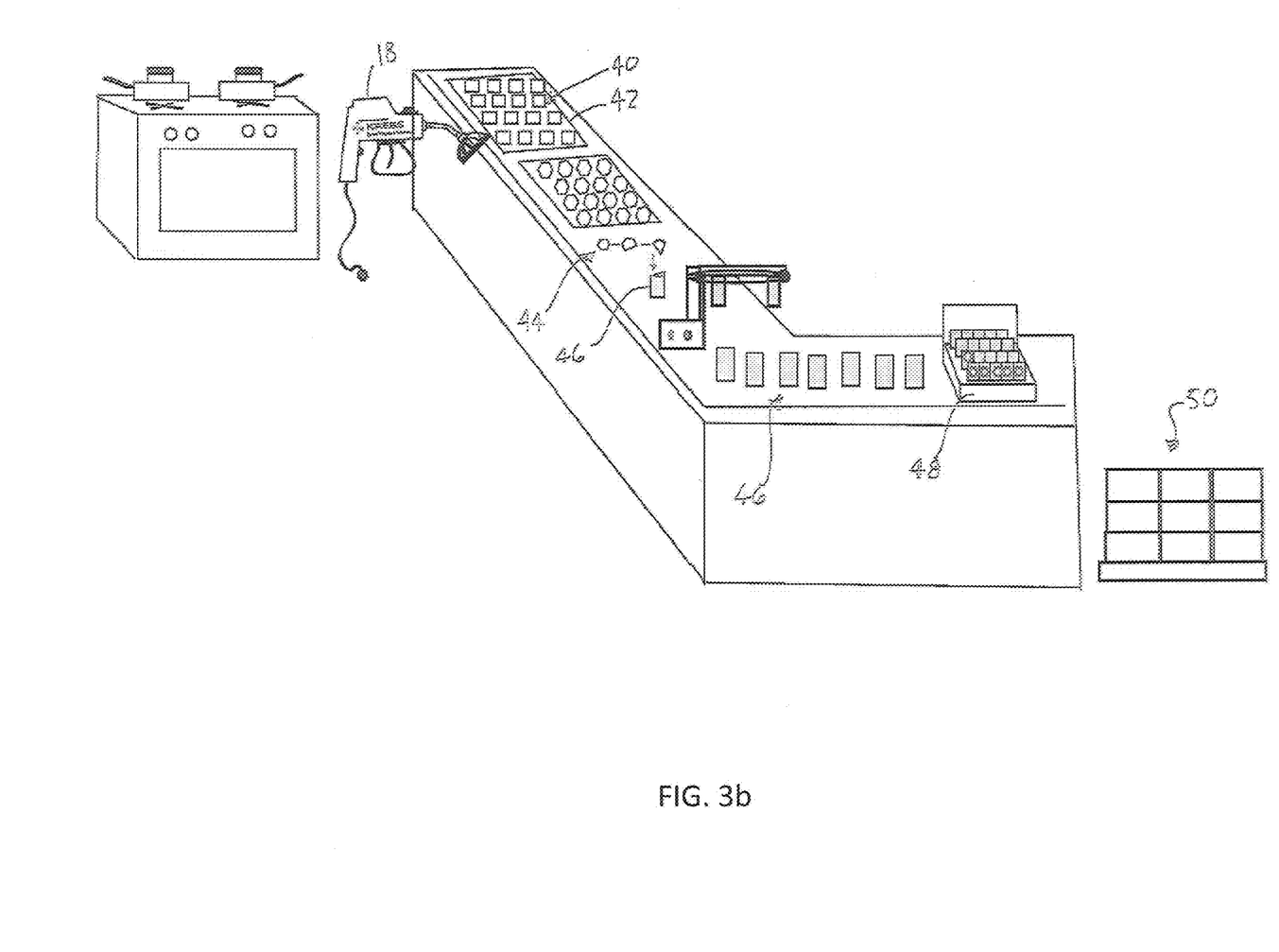
FIG. 3b illustrates an exemplary manual brewing apparatus production line.
Figure 3C:
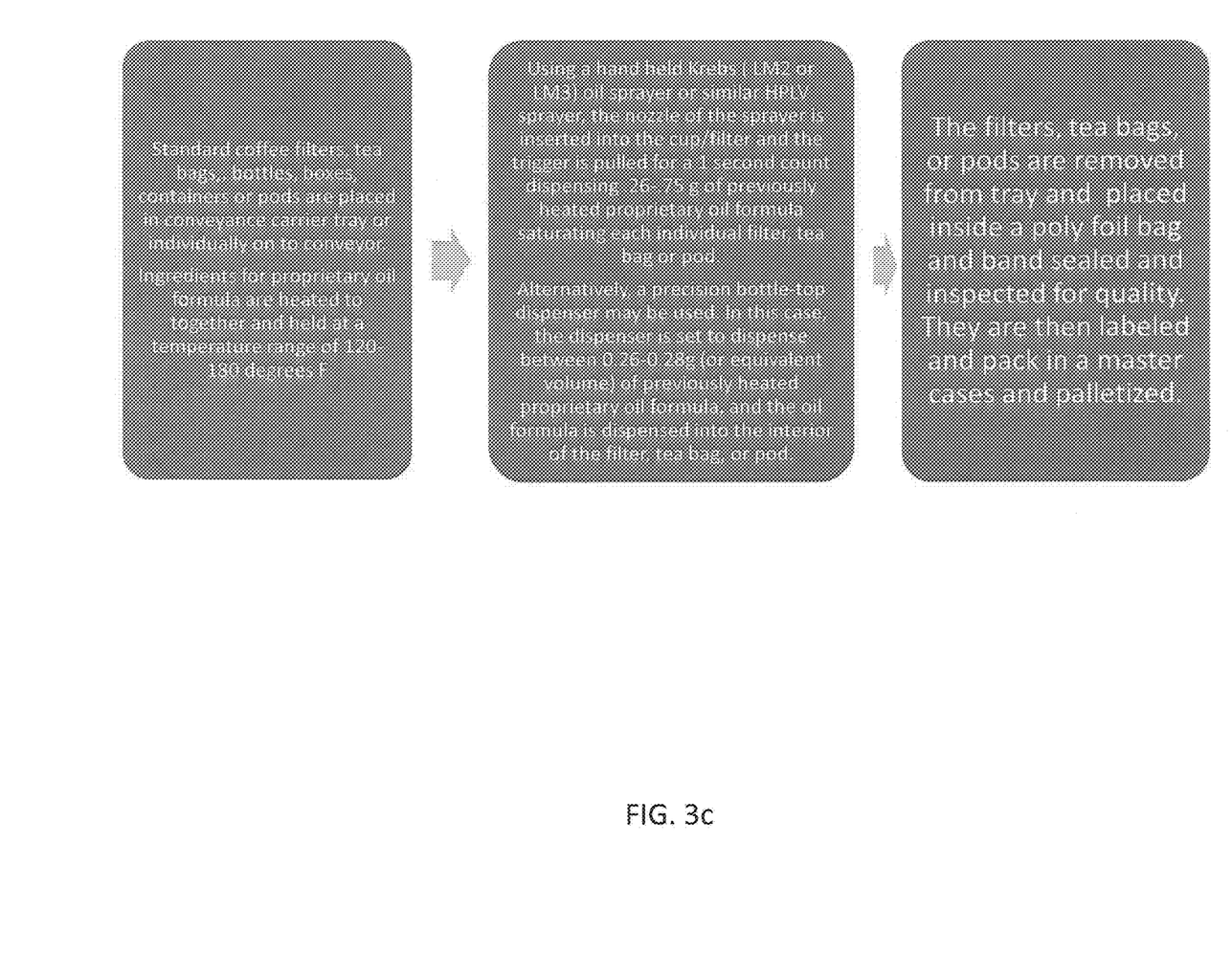
FIG. 3c is a flow chart describing the exemplary production lines of FIGS. 3a and 3b.

As shown in FIGS. 3a and 3b, an example manual coffee filter, tea bags, beverage screen, or pods process and production line is illustrated. FIG. 3c shows the processes illustrated in FIGS. 3a and 3b. Standard coffee filters, tea bags, beverage screens, and/or pods 40 may be placed in a conveyance carrier tray 42. The oil-based solution may be prepared as discussed above. The oil-based solution may be placed in a holder or reservoir (e.g., the reservoir of a spraying apparatus). Then, using a spraying apparatus 18 (such as, for example, a Krebs brand LM2 or LM3, as illustrated in FIG. 3a), the nozzle of the spraying apparatus 18 may be positioned over the filter, tea bag or pod 40 and the trigger may be pulled for a 1 second count, thereby dispensing 0.26-0.75 g of the oil-based solution and saturating each individual filter, tea bag or pod 40 to produce treated filters, tea bags or pods 44. In an alternate embodiment, the spraying apparatus 18 may be a precision bottle-top dispenser. In such an embodiment, the oil-based solution may be placed in a bottle, which could be affixed with a precision bottle-top dispenser. The precision bottle-top dispenser, as the spraying apparatus 18, could be pre-set to dispense between 0.26-0.75 g, for example, of the oil-based solution into or onto the individual filters, tea bags, or pods 40 when toggled by a user. The treated filters, tea bags or pods 44 may be removed from the tray 42 and placed inside a poly foil bag 46, which may be band sealed and inspected for quality. The sealed bags 46 may then be labeled and packed in master cases 48 and palletized 50.

Figure 4A:
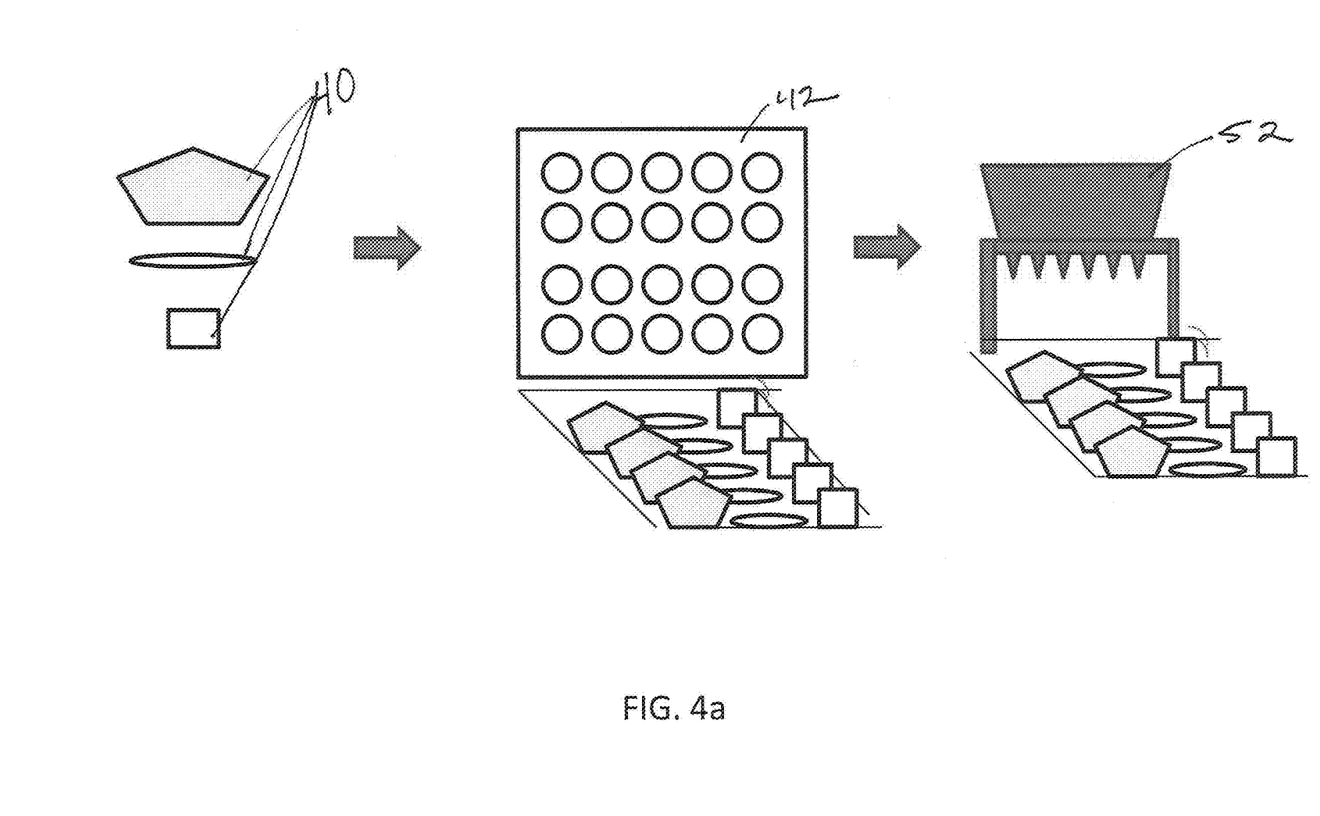
FIG. 4a illustrates a portion of an exemplary automatic brewing apparatus production line.
Figure 4B:
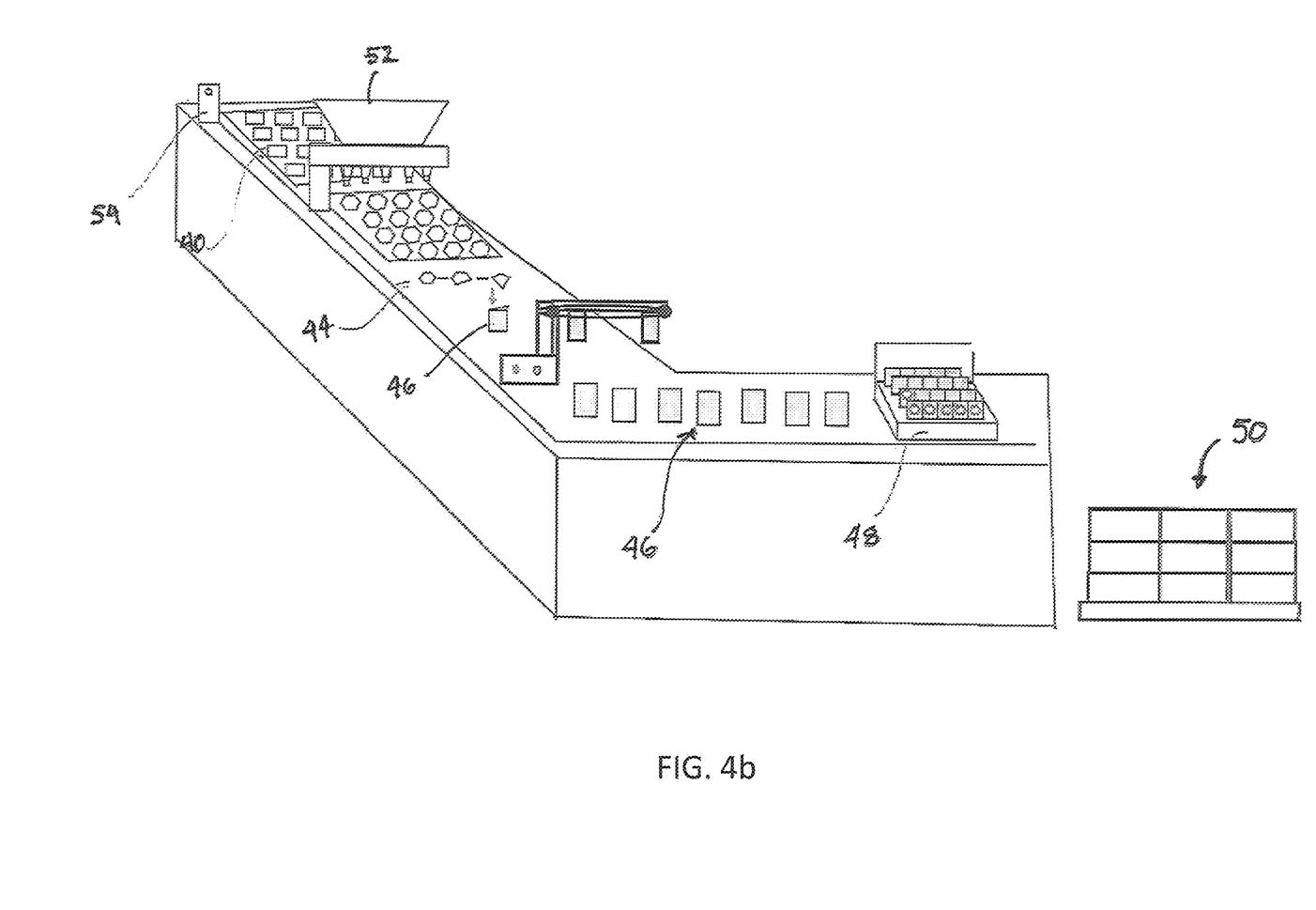
FIG. 4b illustrates an exemplary automatic brewing apparatus production line.
Figure 4C:
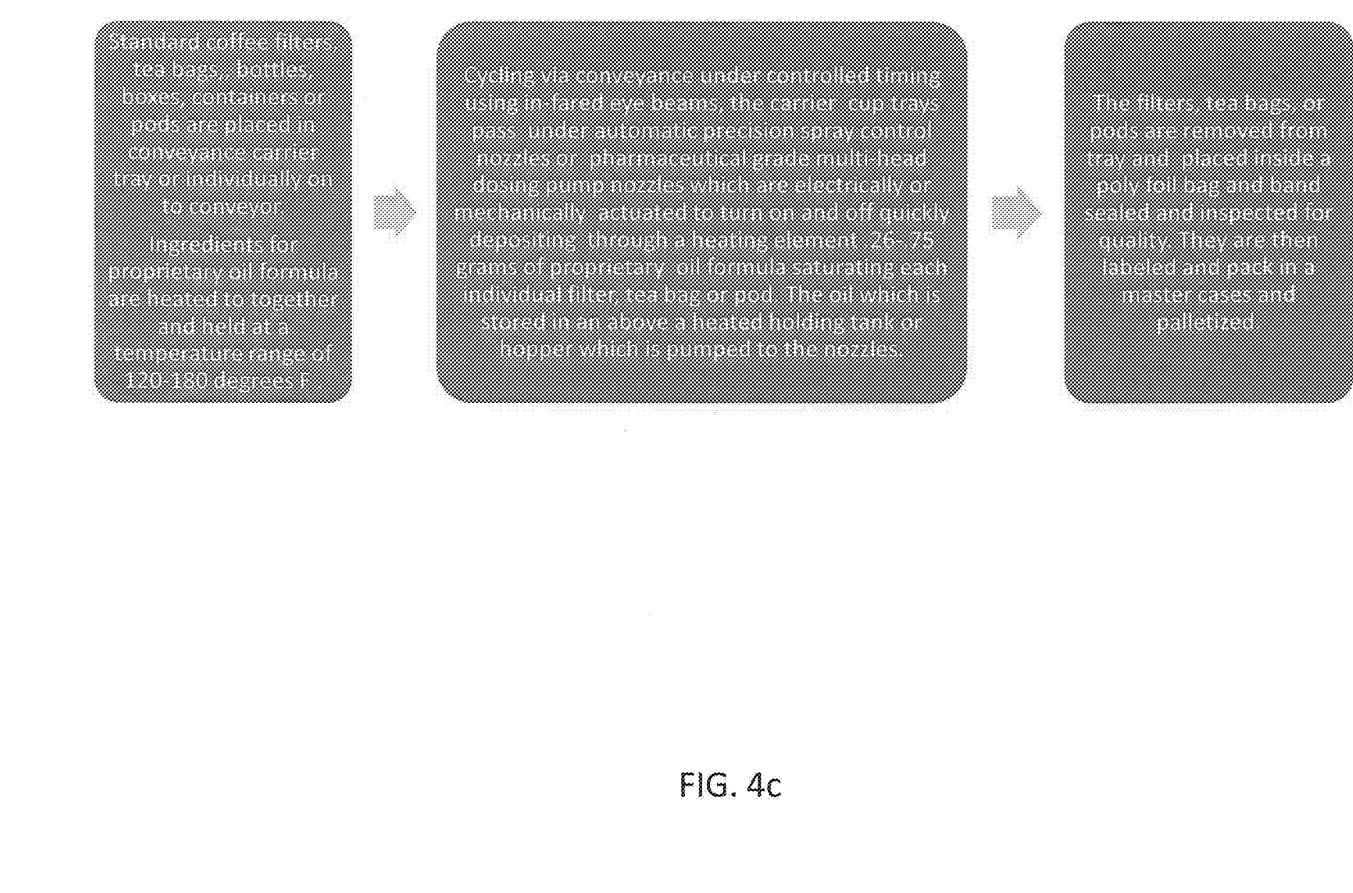
FIG. 4c is a flow chart describing the exemplary production line of FIGS. 4a and 4b.

As shown in FIG. 4a and FIG. 4b, an example automated coffee filter, tea bags, or pods production line is illustrated. FIG. 4c provides a flow chart describing the example production line of FIGS. 4a and 4b. Standard coffee filters, tea bags and/or pods 40 may be placed in a conveyance carrier tray 42. The oil-based solution may be prepared as discussed above. Using an automatic precision spray control depositor 52, the oil-based formulation at the proper temperature and application rate may be applied to the coffee filters, tea bags and/or pods 40. An infrared eye timing beam 54 may be used to signal the electrically actuated nozzles of the depositor 52 at an appropriate timing rate based upon a sensed movement of the conveyor. The treated filters, tea bags or pods 44 may be removed from the tray 42 and placed inside a poly foil bag 46, which may be band sealed and inspected for quality. The sealed bags 46 may then be labeled and packed in master cases 48 and palletized 50.

In any of the above-described production lines, instead of coffee filters, tea bags, or pods, beverage screens may be produced for use in a concentrated drink flavoring container, for example, the concentrated drink flavoring containers that may be used in the SodaStream™ systems. One of skill in the art will recognize that treating the beverage screens with the oil-based solution may proceed in the same manner as treating coffee filters, tea bags, or pods. The container may be filled with concentrated liquid flavoring, after which the beverage screen may be installed at or near the cap or opening such that a user pours the concentrated liquid flavoring through the beverage screen in use. The containers may be capped and sealed, labeled, and packed in cases and palletized.

The current disclosure envisions many possible options for the pharmaceutical, holistic or medicinal component in the oil-based solution. The current disclosure briefly discusses each of the following groups (pharmaceutical, medical, and holistic) and provides examples of each group that may be included in the oil-based solution.

The pharmaceuticals group includes a potential list of ingredients. Depending on the application, one pharmaceutical ingredient may be preferred over another (e.g., based on the condition being treated). However, any of the following pharmaceuticals could be added to the oil-based solution and be infused via spraying process on beverage filters and paired with an appropriate beverage that will offer a safe and effective vehicle for the pharmaceutical, such as beverages, coffee, teas, decaffeinated coffee, hot chocolate and or ciders. The pharmaceuticals may be used appropriately in a proprietary oil formula, independently or in combination, based on FDA approved medical research for the "relief of" or proven "cure" for certain diseases and ailments. The pharmaceuticals group may include one, some or all of the following:
1. Antipyretics
2. Analgesics
3. Antimalarials 4. Antibiotics
5. Mood Stabilizers
6. Hormone Replacements
7. Stimulants
8. Tranquilizers
9. Statins
10. Antacids
11. Reflux Suppressants
12. Antiflatulents
13. Antidopaminergics
14. Proton Pump Inhibitors (PPIS)
15. $H_2$-Receptor Antagonists
16. Cytoprotectants
17. Prostaglandin Analogues
18. Laxatives
19. Antispasmodics
20. Antidiarrhoeals
21. Bile Acid Sequestrants
22. Opioids
23. B-Receptor Blockers ("Beta Blockers")
24. Calcium Channel Blockers
25. Diuretics
26. Cardiac Glycosides
27. Antiarrhythmics
28. Nitrates
29. Antianginals
30. Vasoconstrictors
31. Vasodilators
32. ACE Inhibitors
33. Angiotensin Receptor Blockers
34. Beta-Blockers
35. A Blockers
36. Thiazide Diuretics
37. Loop Diuretics
38. Aldosterone Inhibitors
39. Coagulation
40. Anticoagulants
41. Heparin
42. Antiplatelet Drugs
43. Fibrinolytics
44. Anti-Hemophilic Factors
45. Haemostatic Drugs
46. HMG-Coa Reductase Inhibitors
47. Hypolipidaemic Agents
48. Psychedelics
49. Hypnotics
50. Anaesthetics
51. Antipsychotics
52. Antidepressants (Including Tricyclic Antidepressants, Monoamine Oxidase Inhibitors, Lithium Salts, And Selective Serotonin Reuptake Inhibitors (SSRIS))
53. Antiemetics
54. Anticonvulsants/Antiepileptics
55. Anxiolytics
56. Barbiturates
57. Movement Disorder (E.G., Parkinson's Disease) Drugs
58. Stimulants (Including Amphetamines)
59. Benzodiazepines
60. Cyclopyrrolones
61. Dopamine Antagonists
62. Antihistamines
63. Cholinergics
64. Anticholinergics
65. Emetics
66. Cannabinoids
67. 5-HT (Serotonin) Antagonists
68. Analgesic Drugs
69. Nsaids (Including COX-2 Selective Inhibitors)
70. Muscle Relaxants
71. Neuromuscular Drugs
72. Anticholinesterases
73. Bronchodilators
74. Antitussives
75. Mucolytics
76. Decongestants
77. Corticosteroids
78. Beta2-Adrenergic Agonists
79. Anticholinergics
80. Mast Cell Stabilizers
81. Leukotriene Antagonists
82. Androgens
83. Antiandrogens
84. Estrogens
85. Gonadotropin
86. Corticosteroids
87. Human Growth Hormone
88. Insulin
89. Antidiabetics (Sulfonylureas, Biguanides/Metformin, Thiazolidinediones, Insulin)
90. Thyroid Hormones, A
91. Ntithyroid Drugs
92. Calcitonin
93. Diphosponate
94. Vasopressin Analogues
95. Antifungal
96. Alkalinizing Agents
97. Quinolones
98. Cholinergics
99. Antispasmodics
100. 5-Alpha Reductase Inhibitor
101. Selective Alpha-1 Blockers,
102. Sildenafils
103. Fertility Medications
104. Hormonal Contraception
105. Ormeloxifene
106. Haemostatic Drugs
107. Antifibrinolytics
108. Hormone Replacement Therapy (HRT)
109. Bone Regulators
110. Beta-Receptor Agonists
111. Follicle Stimulating Hormone
112. Luteinising Hormone
113. LHRH
114. Gamolenic Acid
115. Gonadotropin Release Inhibitor
116. Progestogen
117. Dopamine Agonists
118. Oestrogen
119. Prostaglandins
120. Gonadorelin
121. Clomiphene
122. Tamoxifen
123. Diethylstilbestrol
124. Antifungals
125. Antileprotics
126. Antituberculous Drugs
127. Antimalarials
128. Anthelmintics
129. Amoebicides
130. Antivirals
131. Antiprotozoals
132. Probiotics
133. Prebiotics 134. Vaccines
135. Immunoglobulins
136. Immunosuppressants
137. Interferons
138. Monoclonal Antibodies
139. Anti-Allergics
140. Antihistamines
141. Corticosteroids
142. Electrolytes
143. Mineral Preparations (Including Iron Preparations And Magnesium Preparations)
144. Parenteral Nutritions
145. Vitamins
146. Anti-Obesity Drugs
147. Anabolic Drugs
148. Haematopoietic Drugs
149. Food Product Drugs
150. Cytotoxic Drugs
151. Therapeutic Antibodies
152. Sex Hormones
153. Aromatase Inhibitors
154. Somatostatin Inhibitors
155. Recombinant Interleukins
156. G-CSF
157. Erythropoietin While there are thousands of different drugs, all marketed drugs fall under one or more tiers of the American Hospital Formulary Service (AHFS) Pharmacologic-Therapeutic Classification System. This classification was developed and is maintained by the American Society of Health-System Pharmacists (ASHP), a national association of pharmacists. The classification includes the following groups of medicines:

1. Antihistamine Drugs (including the prescription drugs Clarinex and Xyzal and OTC medicines Allegra, Benadryl, Claritin, Chlor-Trimeton, Dimetane, Zyrtec and Tavist)
2. Anti-infective Agents (including penicillins and antivirals)
3. Antineoplastic Agents
4. Autonomic Drugs
5. Blood Derivatives
6. Blood Formation, Coagulation, and Thrombosis Agents
7. Cardiovascular Drugs (including digoxin, acebutolol, propranolol and lisinopril)
8. Cellular Therapy
9. Central Nervous System (CNS) Agents (including stimulants and depressants)
10. Contraceptives
11. Dental Agents
12. Diagnostic
13. Electrolytic, Caloric, and Water Balance
14. Enzymes
15. Respiratory Tract Agents
16. Eye, Ear, Nose, and Throat (EENT) Preparations
17. Gastrointestinal Drugs (including rabeprazole sodium, nitazoxanide, bevacizumab and nizatidine)
18. Gold Compounds
19. Heavy Metal Antagonists
20. Hormones and Synthetic Substitutes
21. Local Anesthetics
22. Oxytocics
23. Radioactive Agents
24. Serums, Toxoids, and Vaccines
25. Skin and Mucous Membrane Agents
26. Smooth Muscle Relaxants (including cyclobenzaprine and carisoprodol)
27. Vitamins
28. Miscellaneous Therapeutic Agents
29. Pharmaceutical Aids The holistic group includes a potential list of ingredient, several of which are listed below. The holistic group may include herbal, vitamin, and/or mineral (single or in combination) additives as a remedy for disease and/or pain (mental, physical, or emotional), or discomfort by way of tinctures; essential oils; plant, flower or root extracts; cell salts; sarcodes; nosodes; and vitamins, to name a few. The holistic group may include ingredients used in naturopathic medicine, traditional Chinese and Eastern medicines, and Ayurvedic medicine. This category may also include non-vitamin supplements, such as fish oil, Omega-3 fatty acid, glucosamine, chondroitin, or flaxseed oil. The holistic group may include one or more of the following ingredients:

1. *Ginkgo biloba*
2. *Hypericum perforatum*
3. Herbal pollen extract NOS
4. *Senna alexandrina*
5. Herbal extract NOS
6. *Cimicifuga racemosa*
7. *Echinacea purpurea*
8. *Plantago ovata*
9. *Serenoa repens*
10. *Glycine max*
11. *Oenothera biennis*
12. *Vitis vinifera*
13. *Cannabis sativa*
14. *Cannabis indica*
15. *Mentha* x *piperita*
16. *Citrus* x *paradisi*
17. *Valeriana officinalis*
18. *Silybum marianum*
19. *Viscum album*
20. *Allium sativum*
21. *Vitex agnus-castus*
22. *Pelargonium reniforme* root
23. *Digitalis purpurea*
24. *Ginseng* NOS
25. Humic acid
26. Vitamin A, B-6, B-12,C, D, E, K
27. Chromium
28. Folic acid
29. Calcium
30. Iron
31. Zinc
32. Plant, Fruit and Nut tinctures, concentrates or extracts A user may purchase brew pods, filters, tea bags, screens, and the like and brew beverages at the user's convenience, for example, by using a conventional coffee brewer at home. Alternatively, the brew pods, filters, tea bags, screens, and the like may be used to create beverages (such as pre-bottled or canned, ready-to-drink beverages) available for individual purchase by a user at a store, vending machine, and the like. Alternatively, a previously-prepared liquid may be run through a filter, bag, or screen treated or prepared with the above-described oil-based solution and then bottled for sale.

Brewing apparatus treated with an oil-based solution containing a pharmaceutical, holistic, or medicinal component and methods of producing the same are disclosed in the present disclosure. The present disclosure is not limited strictly to such embodiments. For example, the present disclosure expressly envisions, and the scope of the present disclosure shall include, beverages or fluid foods produced from the disclosed brewing apparatus. For example, a beverage or fluid food may be prepared by performing the steps of: obtaining a brewing filter or screen; preparing an oil-based solution including an edible oil carrier, a food-grade emulsifier, and at least one of a pharmaceutical, holistic, or medicinal component; applying the oil-based solution to the brewing filter or screen; forming a filled brewing filter or screen by inserting a product to be brewed into the brewing filter or screen; and brewing a drinkable liquid by running water through the filled brewing filter or screen. A beverage or fluid food produced by such a process is expressly within the scope of the present disclosure. Of course, one of skill in the art will recognize that such a process used to produce a beverage or fluid food is just an example, and other related embodiments consistent with the entirety of the present disclosure are apparent.

Having described the inventions covered by this disclosure by way of examples and various embodiments, it will be apparent to those of ordinary skill that modifications can be made without departing from the scope of the inventions as claimed herein. Further, it is not intended that any specific embodiment or disclosure be read into the meaning of the claims as recited. Finally, it should be understood that, while objects or advantages of the inventions may be set forth herein, there may be additional objects and advantages that are inherent or not discussed. Therefore, it is not specifically intended that any stated objects or advantages be met to fall within the scope of any of the following claims.

What is claimed is:

1. A beverage (or fluid food) brewing apparatus comprising one of a brewing filter or screen, said brewing filter or screen having an at least 50% lipid oil-based solution applied thereon, wherein the oil-based solution includes:
   50-80% of a food grade lipid component;
   2-20% of emulsifier and stabilizer components; and
   4.8-30% of a pharmaceutical, holistic or medicinal component.

2. A beverage (or fluid food) brewing apparatus comprising one of a brewing filter or screen, said brewing filter or screen having an at least 50% lipid oil-based solution applied thereon, wherein the oil-based solution includes:
   50-80% of a lipid;
   1-14% of a polysorbate;
   1-6% of a sorbitan stearate; and
   4.8-30% of a pharmaceutical, holistic or medicinal component.

3. A beverage (or fluid food) brewing apparatus comprising one of a brewing filter or screen, said brewing filter or screen having an at least 50% lipid oil-based solution applied thereon, wherein the oil-based solution includes:
   50-80% of a lipid;
   1-20% of an extract of *Quillaja saponaria*; and
   4.8-30% of a pharmaceutical, holistic, or medicinal component.

* * * * *